United States Patent
Hong et al.

(10) Patent No.: US 8,377,706 B2
(45) Date of Patent: Feb. 19, 2013

(54) OLFACTORY RECEPTOR-FUNCTIONALIZED TRANSISTORS FOR HIGHLY SELECTIVE BIOELECTRONIC NOSE AND BIOSENSOR USING THE SAME

(75) Inventors: Seung-Hun Hong, Seoul (KR); Tai Hyun Park, Seoul (KR); Tae-Hyun Kim, Seoul (KR); Sang Hun Lee, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 152 days.

(21) Appl. No.: 12/991,609

(22) PCT Filed: May 7, 2009

(86) PCT No.: PCT/KR2009/002401
§ 371 (c)(1),
(2), (4) Date: Nov. 8, 2010

(87) PCT Pub. No.: WO2009/136742
PCT Pub. Date: Nov. 12, 2009

(65) Prior Publication Data
US 2011/0059544 A1 Mar. 10, 2011

(30) Foreign Application Priority Data

May 7, 2008 (KR) ......................... 10-2008-0042373
May 6, 2009 (KR) ......................... 10-2009-0039471

(51) Int. Cl.
*G01N 25/18* (2006.01)
(52) U.S. Cl. ............. 436/149; 436/151; 422/50; 422/98

(58) Field of Classification Search .................... None
See application file for complete search history.

(56) References Cited

U.S. PATENT DOCUMENTS
(Continued)

FOREIGN PATENT DOCUMENTS

| KR | 100736361 | 7/2007 |
|---|---|---|
| KR | 1020080003670 | 1/2008 |

(Continued)

OTHER PUBLICATIONS

Yoon, H., et al, Polypyrrole Nanotubes Conjugated with Human Olfactory Receptors: High-Performance Transducers for FET-Type Bioelectronic Noses, Mar. 9, 2009, Angew. Chem. Int. Ed., vol. 48, pp. 2755-2758.*

Tang, X., et al. Carbon nanotube DNA sensor and sensing mechanism, 2006, Nano Letters, vol. 6(8), pp. 1632-1636.*

(Continued)

*Primary Examiner* — Robert Xu
(74) *Attorney, Agent, or Firm* — IP & T Group LLP (57) ABSTRACT

In accordance with an aspect of the present invention, there is provided a transistor including: a substrate; a source electrode and a drain electrode formed being spaced apart from each other on the substrate; a nanostructure electrically contacted with and formed between the source electrode and the drain electrode; and a lipid membrane having an olfactory receptor protein which is formed to cover surfaces of the source electrode, the drain electrode, and the nanostructure. The olfactory receptor-functionalized transistor in accordance with an aspect of the present invention is useful for a bioelectronic nose which can detect odorants highly specifically with femtomolar sensitivity, and may be applied in various fields requiring the rapid detection of specific odorants, for example, anti-bioterrorism, disease diagnostics, and food safety.

20 Claims, 8 Drawing Sheets

U.S. PATENT DOCUMENTS

| | | |
|---|---|---|
| 7,342,479 B2 | 3/2008 | Glatkowski et al. |
| 2006/0104864 A1 | 5/2006 | Fu |
| 2006/0204428 A1 | 9/2006 | Noy et al. |

FOREIGN PATENT DOCUMENTS

| | | |
|---|---|---|
| KR | 1020080005303 | 1/2008 |
| KR | 1020090060657 | 6/2009 |
| WO | WO 2006/110347 | 10/2006 |

OTHER PUBLICATIONS

Vidic, J. Bioelectronic noses based on olfactory receptors, 2010, Intelligent and Biosensors, Edited by Vermon S. Somerset, pp. 377-386.*

Tae Hyun Kim et al., "Single-Carbon-Atomic-Resolution Detection of Odorant Molecules using a Human Olfactory Receptor-based Bioelectronic Nose," Adv. Mater. 2009, Oct. 30, 2008, pp. 91-94, vol. 21.

* cited by examiner

OLFACTORY RECEPTOR-FUNCTIONALIZED TRANSISTORS FOR HIGHLY SELECTIVE BIOELECTRONIC NOSE AND BIOSENSOR USING THE SAME

This application is a national stage application of PCT/KR2009/002401 filed on May 7, 2009, which claims priority of Korean patent application number 10-2008-0042373 filed on May 7, 2008 and Korean patent application number 10-2009-0039471 filed on May 6, 2009. The disclosure of each of the foregoing applications is incorporated herein by reference in its entirety.

TECHNICAL FIELD

The present invention relates to a transistor and a biosensor using the same and, more particularly, to an olfactory receptor-functionalized transistor useful for a highly selective bioelectronic nose, and a biosensor using the same.

BACKGROUND ART

Recently, interests have been concentrated on sensors which can detect and analyze a target material using nanomaterials in various application fields. In particular, portable nano-sensor systems for the rapid detection of specific odorants play important roles in anti-bioterrorism, disease diagnostics, and food safety.

Since the first report of "electronic nose" in relation to this, there have been many efforts to develop artificial olfactory sensors based on the arrays of semiconductor devices. "Electronic nose" refers to a system which may reproduce a human nose using sensor arrays and pattern recognition systems. However, the capabilities of the electronic noses thus developed are still inferior to those of the human olfactory system in terms of specificity.

In the smelling process of the human olfactory system, the initial step is to bind specific odorants to the olfactory receptor protein which triggers signal transduction in a cell. Olfactory receptors expressed in the cell membranes of olfactory receptor neurons are responsible for the detection of odorant molecules. That is, when the odorants bind to the olfactory receptors as described above, the receptors are activated. The activated olfactory receptors are the initial player in a signal transduction cascade which ultimately produces a nerve impulse which is transmitted to the brain. These olfactory receptors are members of the class A rhodopsin-like family of G protein-coupled receptors (GPCRs).

Over the last decade, the development of bioelectronic noses with olfactory receptors as a sensing part has been a major concern. In addition, various technologies such as quartz-crystal microbalance, electrochemical impedance spectrometry, surface plasmon resonance, and light-addressable potentiometric sensor have been used as a transducer part of the bioelectronic nose. However, these technologies have problems such as big system size and limited sensitivity.

Various transistors based on nano-structures, particularly single-walled carbon nanotube-field effect transistors (swCNT-FETs) have been widely studied in the high-selectivity biosensor, but swCNT-FETs have not been used in the application of the bioelectronic nose. This is partly because olfactory receptors are G protein-coupled receptors (GPCRs) which may maintain their functionality only as a part of the cell membranes, as described above. Thus, unlike other receptor molecules which may exist alone and be easily connected with the surface of the transducer, lipid membranes containing functional olfactory receptors should be formed on swCNT-FETs to build a bioelectronic nose, which is still a very difficult task.

DISCLOSURE

Technical Problem

An embodiment of the present invention is directed to providing an olfactory receptor-functionalized transistor useful for a bioelectronic nose which may detect and analyze specific odorants with high selectivity by functionalizing a nanostructure transistor with an olfactory receptor, a method for manufacturing the transistor, a biosensor using the same, and a method for detecting odorants using the biosensor.

Other objects and advantages of the present invention can be understood by the following description, and become apparent with reference to the embodiments of the present invention. Also, it is obvious to those skilled in the art of the present invention that the objects and advantages of the present invention can be realized by the means as claimed and combinations thereof.

Technical Solution

In accordance with an aspect of the present invention, there is provided a transistor including: a substrate; a source electrode and a drain electrode formed being spaced apart from each other on the substrate; a nanostructure electrically contacted with and formed between the source electrode and the drain electrode; and a lipid membrane having an olfactory receptor protein which is formed to cover surfaces of the source electrode, the drain electrode, and the nanostructure.

In accordance with another aspect of the present invention, there is provided a method for manufacturing a transistor including: forming a nanostructure on a substrate; forming a source electrode and a drain electrode to be spaced apart from each other and electrically contact the nanostructure on the substrate; and forming a lipid membrane having an olfactory receptor protein to cover surfaces of the nanostructure, the source electrode, and the drain electrode.

In accordance with another aspect of the present invention, there is provided a biosensor for detecting odorants to be bound to the olfactory receptor protein by using the transistor.

In accordance with another aspect of the present invention, there is provided a method for detecting odorants using the biosensor, the method including: exposing odorants to the biosensor; and measuring a conductance modulation generated by binding the odorants to the olfactory receptor protein of the biosensor.

Advantageous Effects

In accordance with an embodiment of the present invention, the significantly improved selectivity and sensitivity in detection of odorants may be achieved by functionalizing a nanostructure transistor with an olfactory receptor.

The olfactory receptor-functionalized transistor is a biosensor useful for a bioelectronic nose which can detect odorants highly specifically with femtomolar sensitivity, and may be applied in various fields requiring the rapid detection of specific odorants, for example, anti-bioterrorism, disease diagnostics, and food safety.

In accordance with an embodiment of the present invention, large-scale and diverse sensor arrays for sensitive and selective multiplexed detection of various odorants may be also realized with a rapid and high-throughput. Furthermore, the present invention may provide a novel and powerful platform for development of novel pharmaceuticals and perfumes based on the capability of monitoring GPCR operation in real time.

BEST MODE FOR THE INVENTION

The advantages, features and aspects of the invention will become apparent from the following description of the embodiments with reference to the accompanying drawings, which is set forth hereinafter.

In one embodiment of the present invention, a transistor includes a substrate; a source electrode and a drain electrode formed being spaced apart from each other on the substrate; a nanostructure electrically contacted with and formed between the source electrode and the drain electrode; and a lipid membrane having an olfactory receptor protein which is formed to cover surfaces of the source electrode, the drain electrode, and the nanostructure.

In the embodiment, the lipid membrane having an olfactory receptor protein is formed to wholly cover the surfaces of the source and drain electrodes formed on the substrate and the surface of the nanostructure formed between the electrodes.

The olfactory receptor protein belongs to a family of G-protein coupled receptors and may exist over the surface of, the interior of, or the surface and interior of a lipid double membrane.

An olfactory receptor membrane generally includes an ionizable cysteine residue and exists in a conformational equilibrium between biophysically activated and non-activated states. The activated and non-activated states of the olfactory receptor molecule are associated with a negatively-charged base form and a neutral acid form of cysteine, respectively.

When specific odorants bind to olfactory receptor molecules, the equilibrium of the receptor molecules moves to an activated receptor form having negative charges. The negative charges of the olfactory receptor molecules which were changed into an activated state modulate the contact resistance between metal electrode and nanostructure, leading to a reduction in conductance.

In accordance with the embodiment of the present invention, odorant molecules may be detected highly selectively based on electrostatic perturbation of a nanostructure junction generated from a conformational change by binding the odorants to the olfactory receptor molecules.

In addition, the olfactory receptor proteins are the largest family of GPCR which is the most ubiquitous class of drug targets and up to 50% of current drugs are targeted at GPCR. Thus, a highly-specific detection of odorants with femtomolar sensitivity may be achieved in real time, and various and novel applications such as a highly selective artificial nose application and development of novel pharmaceuticals and perfumes may be achieved.

In one embodiment of the present invention, the nanostructure may be at least one form selected from the group consisting of nanotube, nanowire, nanorod, nanoribbon, nanofilm, and nanoball.

For example, semiconductor nanowires such as silicon nanowires, and carbon nanotubes may be used, and a single-walled carbon nanotube is especially preferable in terms of high biocompatibility and device characteristics.

The substrate may be at least one selected from the group consisting of silicon, glass, quartz, metal, plastic and oxide.

The source and drain electrodes may be formed of at least one metal selected from the group consisting of platinum, gold, chrome, copper, aluminum, nickel, palladium, and titanium.

In accordance with another embodiment of the present invention, a method for manufacturing a transistor includes forming a nanostructure on a substrate; forming a source electrode and a drain electrode to be spaced apart from each other and electrically contact the nanostructure on the substrate; and forming a lipid membrane having an olfactory receptor protein to cover surfaces of the nanostructure, the source electrode, and the drain electrode.

Said forming a nanostructure on the substrate may include patterning a self-assembled monolayer consisting of a molecule with a interface energy to the nanostructure higher than that of the substrate surface, on the substrate surface, immersing or exposing the patterned substrate in a nanostructure-containing solution or to a nanostructure-containing gas, and selectively adsorbing the nanostructure on a bare surface portion of the substrate on which the self-assembled monolayer is not formed.

Non-limiting examples for forming the nanostructure are described in Korean Patent No. 10-736361, which is hereby incorporated by reference.

Said forming a lipid membrane having an olfactory receptor protein to cover surfaces of the nanostructure, the source electrode, and the drain electrode may include spreading a solution of lipid membrane having the olfactory receptor protein on surfaces of the nanostructure, the source electrode, and the drain electrode, vacuum-drying the solution, and fixing the olfactory receptor protein.

The lipid membrane having an olfactory receptor protein is hereby formed to wholly cover the surfaces of the source and drain electrodes formed on the substrate and the surface of the nanostructure formed between the electrodes.

In accordance with one embodiment of the present invention, the processes may be applied in detection of odorants by fixing the olfactory receptor protein through reducing complex procedures and simplifying manipulations.

A solution of lipid membrane having the olfactory receptor protein may be a membrane fraction having the olfactory receptor protein.

The time for vacuum drying may be suitably selected to fix the olfactory receptor protein in accordance with manufacturing conditions, and may be, for example, about 1 hour to about 10 hours, preferably about 3 hours to 5 hours.

Referring to FIGS. 1 to 4, a method for manufacturing a transistor 1 is specifically described in accordance with one Example of the present invention.

Figure 1:
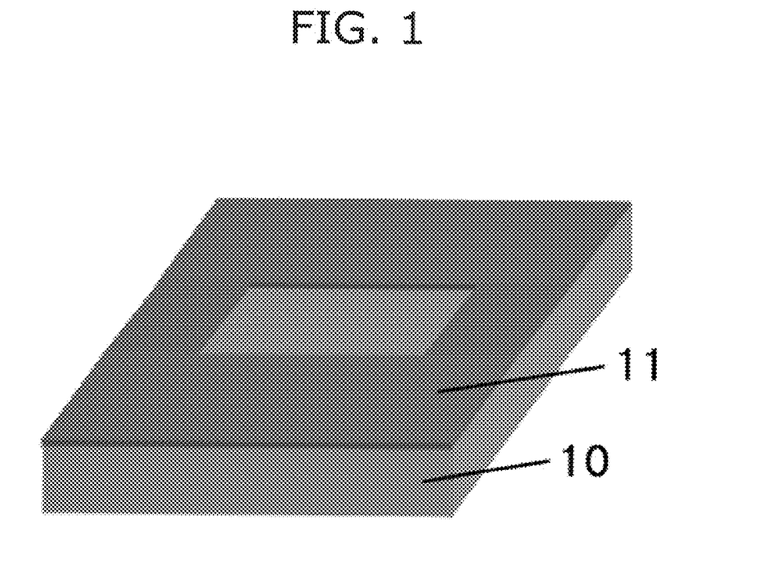
FIGS. 1 to 4 show schematic views of a method for manufacturing a transistor in accordance with one example of the present invention.

First, in order to form a nanostructure 12 on a substrate 10, a self-assembled monolayer 11 consisting of a molecule with interface energy to the nanostructure higher than that of the surface of the substrate 10, on the substrate 10 surface.

For example, when single-walled carbon nanotubes are formed on a $SiO_2$ substrate, a self-assembled monolayer (SAM) consisting of at least one molecule selected from the group consisting of hydrophobic molecules, especially, octadecyltrichlorosilane (OTS), octadecyltrimethoxysilane (OTMS), octadecyltriethoxysilane (OTE), and octadecanethiol (ODT) may be patterned.

The patterning method is not specifically limited, and may include, for example, microcontact printing, photolithography, dip-pen nanolithography, e-beam lithography, ion-beam lithography, nanografting, nanoshaving, or STM lithography.

Figure 2:
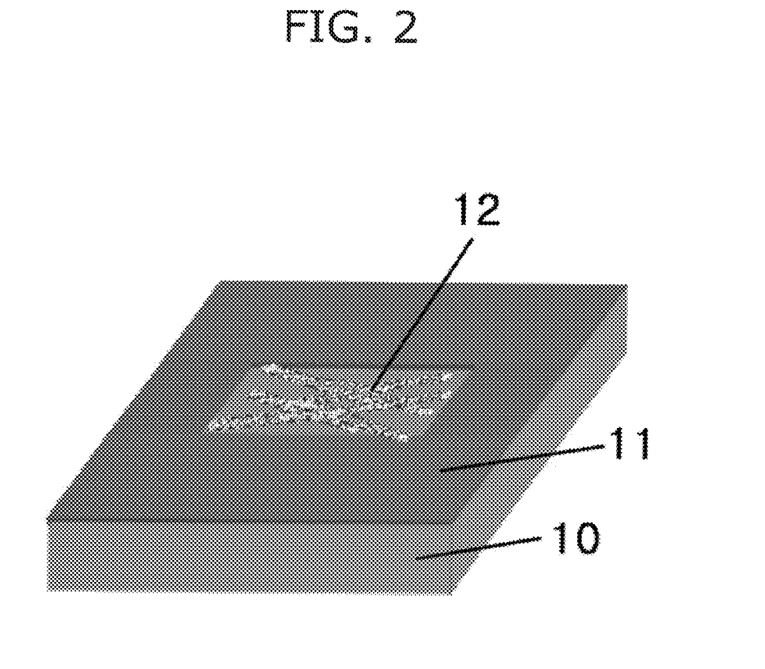

When the thus patterned substrate 10 is immersed in a nanostructure 12—containing solution or exposed to a nanostructure 12—containing gas, a nanostructure 12 may be selectively adsorbed and formed on a bare surface portion of the substrate on which the self-assembled monolayer 11 is not formed, as described in FIG. 2.

Figure 3:
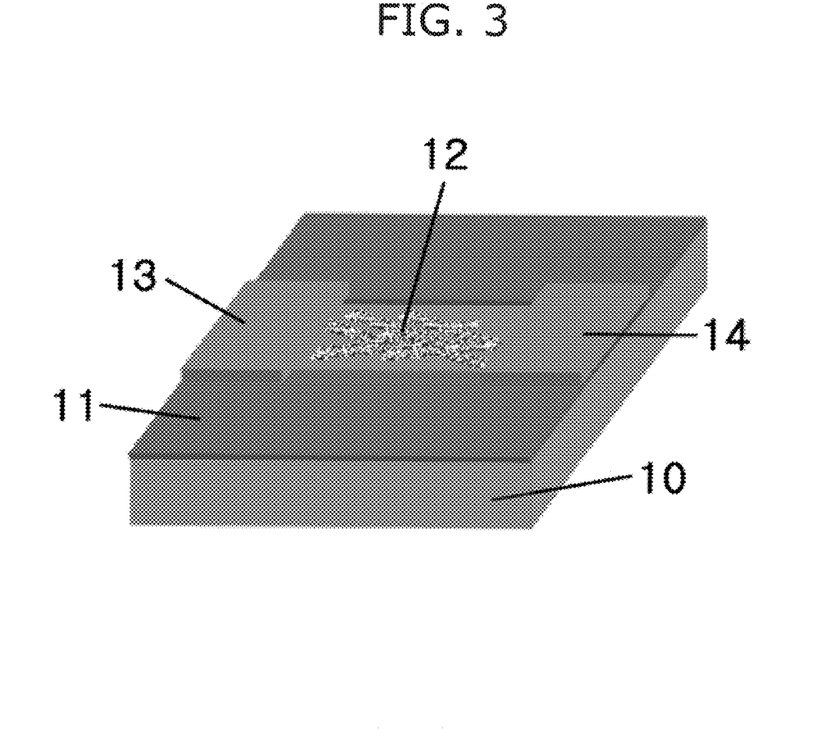

As described in FIG. 3, a source electrode 13 and a drain electrode 14 are formed to be spaced apart from each other and electrically contact the nanostructure 12 formed on the surface of the substrate 10.

The electrode formation method may be appropriately selected from methods generally known in the art, and include photolithography, physical vapor deposition (PVD), e-beam evaporation, or thermal evaporation.

Figure 4:
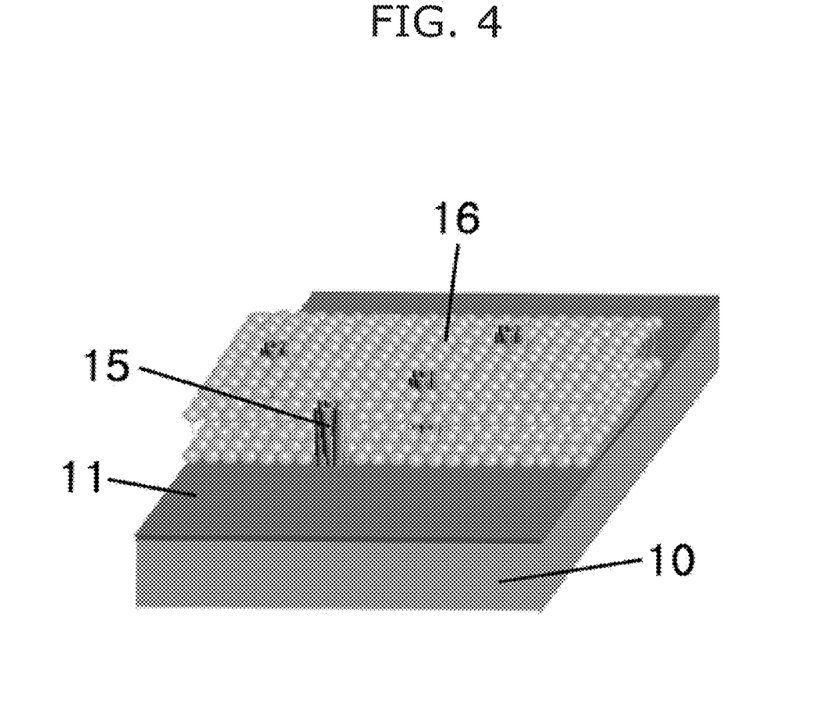

Subsequently, as described in FIG. 4, a lipid membrane 16 having the olfactory receptor protein 15 is formed to cover surfaces of the nanostructure 12, the source electrode 13, and the drain electrode 14. These processes may be achieved by spreading a lipid membrane 16 having the olfactory receptor protein 15—containing solution on surfaces of the nanostructure 12, the source electrode 13, and the drain electrode 14, vacuum-drying the solution, and fixing the olfactory receptor protein 16.

Another embodiment of the present invention relates to a biosensor which detects odorants to be bound to the olfactory receptor protein by using a transistor as described above.

Another embodiment of the present invention also relates to a method for detecting odorants using the biosensor, including exposing odorants to the biosensor of the present invention and measuring a conductance modulation generated by binding the odorants to the olfactory receptor protein of the biosensor.

In the embodiment, said exposing odorants to the biosensor of the present invention may be performed by contacting an odorant-containing solution or an odorant-containing gas with the biosensor.

That is, a method for detecting odorants in accordance with one embodiment includes, after an odorant-containing solution is dripped on and contacted with the biosensor, measuring a conductance modulation generated by binding odorants to the olfactory receptor protein of the biosensor.

In addition, a method for detecting odorants in accordance with embodiment includes, after an odorant-containing gas is exposed to and contacted with the biosensor, measuring a conductance modulation generated by binding odorants to the olfactory receptor protein of the biosensor.

Figure 5:
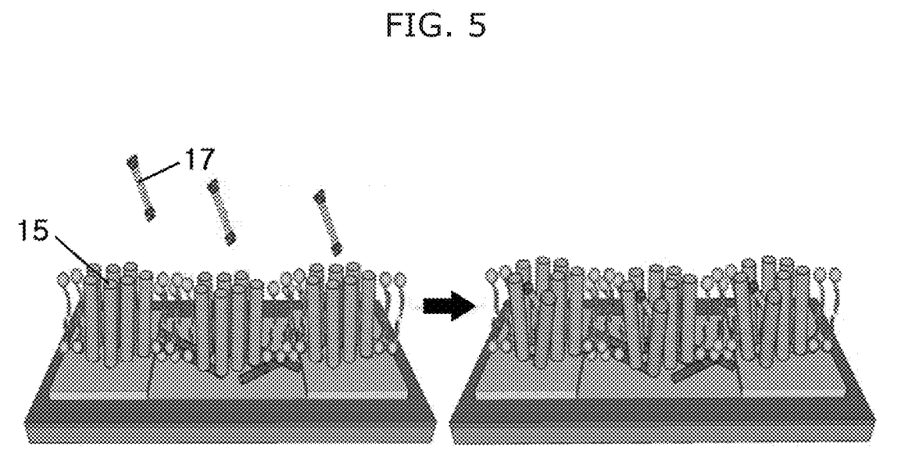
FIG. 5 shows a schematic view of a mechanism for detection of odorants in accordance with one example of the present invention.

As a mechanism described in FIG. 5, when specific odorant 17 binds to an olfactory receptor protein 15, the olfactory receptor protein 15 is changed into an activated receptor form having negative charges. Because the conformational change causes a conductance decrease, the detection of odorants may be achieved by measuring the conductance decrease.

As described above, the olfactory receptor proteins are the largest family of GPCR, at which up to 50% of current drugs are targeted, and thus a detection of odorants with high selectivity, sensitivity, and specificity may be achieved in real time in accordance with the embodiment of the present invention.

EXAMPLE

Example 1

Preparation, Immunoblot Analysis, and Electron Microscopy of an Olfactory Receptor Protein (1) Preparation of Human Olfactory Receptor 2AG1 Protein (hOR2AG1)

As an olfactory receptor protein, human olfactory receptor 2AG1 (hOR2AG1) protein was used. The hOR1AG1 protein is a fusion protein with a glutathione-S-transferase (GST)-tag at the N-terminus, which is expressed in *Escherichia coli* (*E. coli*).

The cultured cells were centrifuged at 7,000 g for 30 min, harvested, and resuspended in 1 ml of phosphate buffered saline (PBS). The resuspended cells were dissolved by an ultrasonic treatment for 5 min, and insoluble fractions including membrane fractions and cell debris were centrifuged at 15,000 g for 30 min and collected. Subsequently, to remove membrane-incorporated proteins other than the hOR1AG1, insoluble fractions including the hOR2AG1 were incubated in a solution containing 2 vol % Triton X-100, and then membrane fractions containing hOR2AG1 were collected by centrifuge.

(2) Immunoblot Analysis of hOR2AG1

The expression of the hOR2AG1 in *E. coli* was identified by a Western Blot Analysis. Insoluble fractions were separated by electrophoresis using sodium dodecylsulfate (SDS)-polyacrylamide gels, and then transferred to a polyvinylidene fluoride membrane (PVDF) (Bio-Rad, CA, USA). The membrane was blocked with 5 wt % skimmed milk in PBS containing 0.1 vol % Tween-20 (PEST, pH 7.4). The membrane was incubated with anti-GST antibody (Santa Cruz, Calif., USA) and antibody conjugated with horseradish peroxidase (Amersham-Pharmacia Biotech, UK). Blots are shown in FIG. 6 by using an enhanced chemiluminescence detection kit (Amersham-Pharmacia Biotech, UK).

Figure 6:
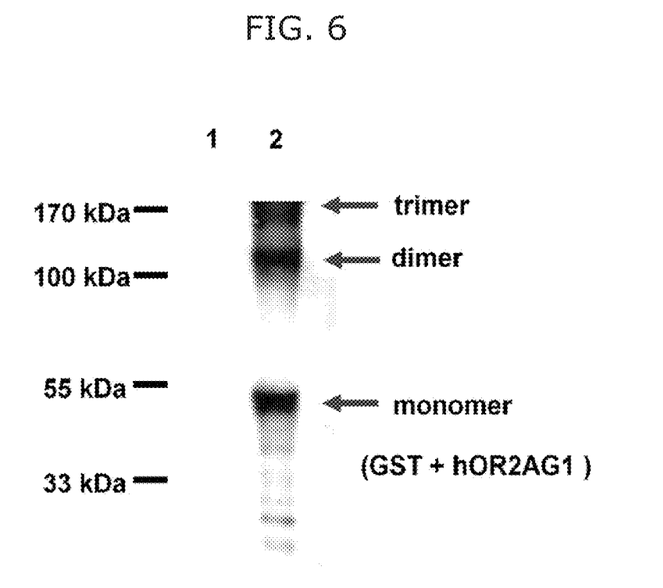
FIG. 6 shows a Western blot analysis of hOR2AG1 in accordance with Example 1.

FIG. 6 shows a Western Blot Analysis to identify the expression of the hOR2AG1 protein, with a cytosol fraction in lane 1 and an insoluble fraction in lane 2. In the Western Blot Analysis in FIG. 6, the protein molecules were bound together as a bimolecular or a trimolecular group in some cases. Polymerized forms such as dimers and trimers occur with monomers of the hOR2AG1. The insoluble fraction may contain a membrane-integrated form and a inclusion body form.

(3) Electron Microscopy of hOR2AG1

To identify the localization of the hOR2AG1 proteins in a cell, *E. coli* cells were fixed with modified Karnovsky's fixative consisting of 0.5 vol % glutaraldehyde and 4 vol % paraformaldehyde in 0.05 M sodium cacodylate buffer (pH 7.2) for 2 hours, and then were embedded in LR white resin. An ultrathin section of *E. coli* (thickness: about 60 nm) loaded on the TEM grid was treated with a blocking solution containing 1 wt % bovine serum albumin (BSA) in tris-buffered saline (TBS, pH 7.2) for 30 min. The grids were incubated in the anti-GST antibody in the blocking solution. After being washed with TBS, they were further treated with an anti-mouse antibody conjugated with 10 nm-colloidal particles (Sigma, Mo., USA). Subsequently, the grids were washed with TBS and stained with 2 wt % uranyl acetate and Reynold's lead citrate. They were examined with a Transmission Electron Microscope operating at accelerating voltage of 120 kV, and an immune gold TEM photograph is shown in FIG. 7.

Figure 7:
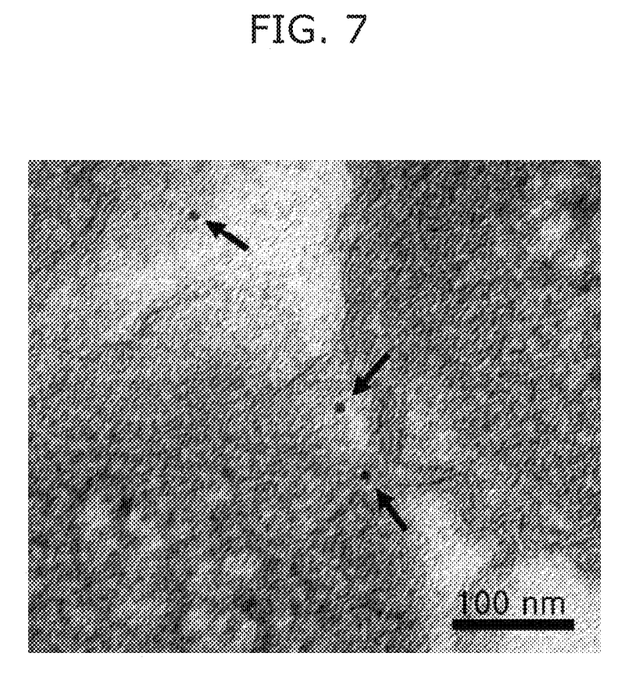
FIG. 7 shows a transmission electron microscope (TEM) photograph of the immunogold-labeled portions of hOR2AG1 in accordance with Example 1.

From FIG. 7, the localization of the hOR2AG1 in *E. coli* cell membranes may be identified.

Example 2

Manufacture of Human Olfactory Receptor-functionalized Transistors

First, purified single-walled carbon nanotubes (swCNTs) (Carbon Nanotechnologies) were dispersed in 1,2-dichlorobenzene with ultrasonic vibration for 20 min to prepare a swCNT suspension. The concentration of the swCNT suspension was 0.1 mg/ml or less.

An octadecyltrichlorosilane (OTS) self-assembled monolayer (SAM) was patterned by photolithography technique on a degenerately doped silicon substrate covered with a 300 nm thick thermal oxide layer. The patterned substrate was put in the swCNT suspension generally for about 10 sec and rinsed with 1,2-dichlorobenzene. The swCNT was selectively adsorbed on a bare portion of the substrate, in which the OTS was not formed. After a typical photolithography, contact electrodes were fabricated by Au/Pd (30 nm/nm) evaporation and lift-off methods. The gap between source and drain electrodes was 4 μm.

1 μl of the hOR2AG1-containing fraction collected in Example 1 was evenly spread to cover the swCNTs and electrodes, and vacuum-dried for 4 hours to fix the hOR2AG1, thereby manufacturing human olfactory receptor-functionalized carbon nanotube transistors.

Example 3

Figure 8:
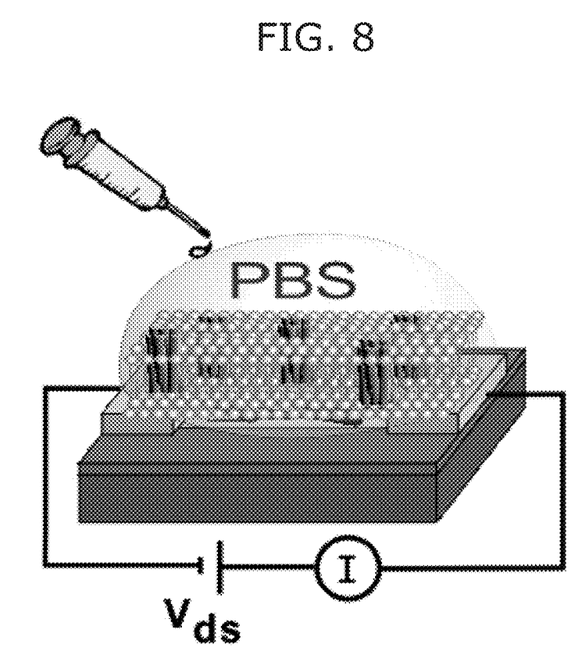
FIG. 8 shows a schematic view of a method for measuring the effects of odorants in accordance with Example 3.

Measurement of Effects of Odorants on Biosensor Using Human Olfactory Receptor-functionalized Transistors of the Present Invention To measure the effects of odorants on the biosensor using human olfactory receptor functionalized transistors, drops of 9 μl phosphate buffered saline (PBS) were placed onto the human olfactory receptor functionalized transistors manufactured in Example 1. Subsequently, the source-drain current was monitored after the introduction of a solution containing specific odorants. A bias voltage of 100 mV was maintained at all time during the electrical measurement (See FIG. 8).

Figure 9:
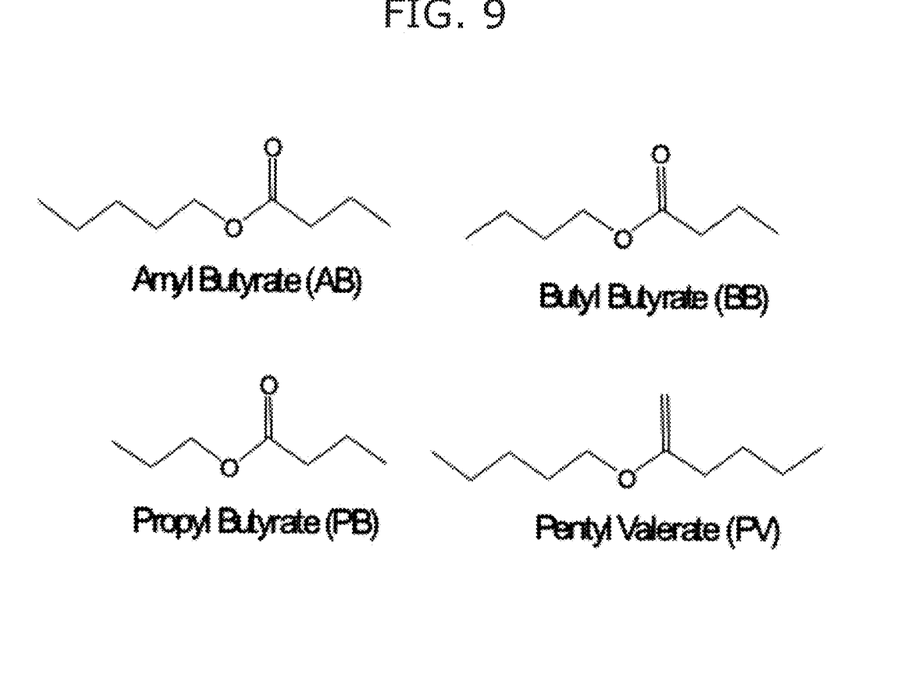
FIG. 9 shows the molecular structures of odorants used in Examples.

FIG. 9 shows four similar odorants (amyl butyrate (AB), butyl butyrate (BB), propyl butyrate(PB), and pentyl valerate (PV)) used for characterization of sensor reactions.

A 1 M stock solution of the odorants was prepared, and additional dilutions (from $10^{-1}$ M to $10^{-13}$ M) were obtained by serial 1:10 dilutions in PBS.

The hOR2AG1 is known to be activated by amyl butyrate (AB), the most common reagent for fruit flavor.

Figure 10:
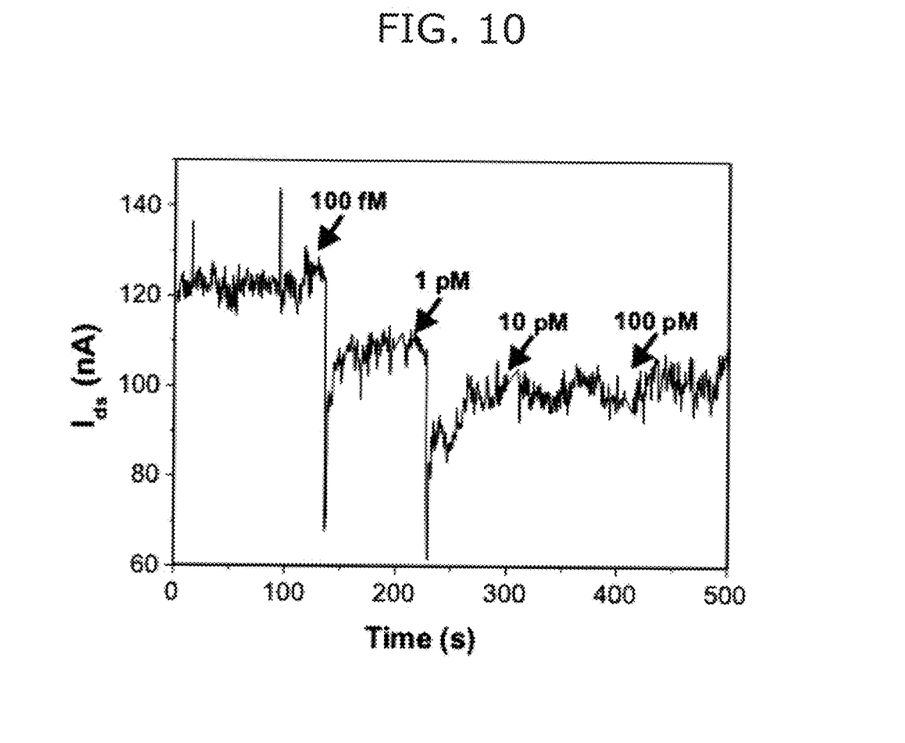
FIG. 10 shows a graph of a real time conductance measurement of the biosensor of the present invention after amyl butyrate was introduced at various concentrations.

FIG. 10 shows a time dependence of the source-drain current of the biosensor after the introduction of amyl butyrate (AB) at various concentrations such as 100 fM, 1 pM, 10 pM, and 100 pM. As described above, the source-drain current was sharply decreased by the addition of amyl butyrate (AB), an odorant known to activate the hOR2AG1, and then gradually saturated at lower values. This indicates that the addition of amyl butyrate (AB) induced the binding of amyl butyrate (AB) to the reactive domain of hOR2AG1, causing a gradual saturation. In accordance with the embodiment of the present invention, the detection of solutions at 100 fM was enabled, meaning that at least 10-fold sensitivity was achieved compared to conventional bioelectronic nose systems using various transducers.

Figure 11:
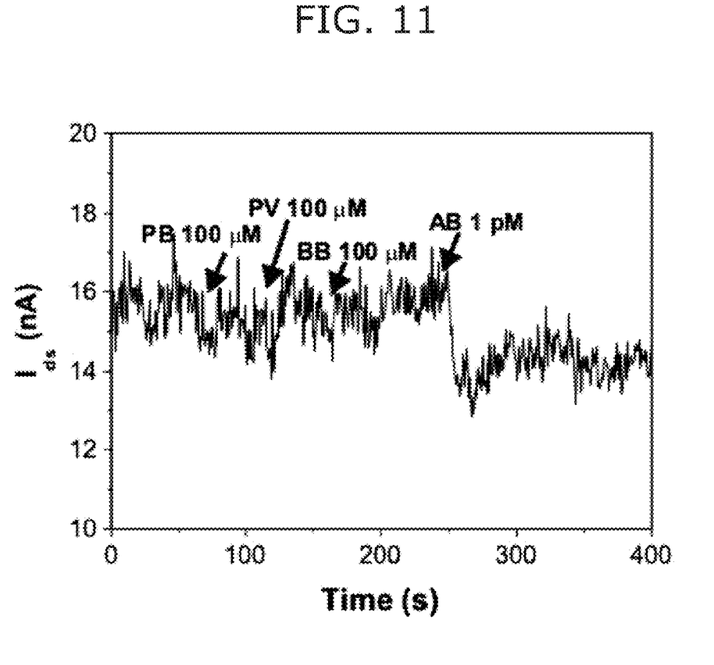
FIG. 11 shows a graph of a real time conductance measurement of the biosensor of the present invention after butyl butyrate, propyl butyrate, and pentyl valerate were introduced at 100 μM and amyl butyrate was introduced at 1 pM.

To illustrate the selectivity of the biosensor, source-drain current changes were measured by introducing other odorants. The arrows illustrated in FIG. 11 indicate the time points at which each of the odorants was introduced. As shown in FIG. 11, butyl butyrate (BB), propyl butyrate (PB), and pentyl valerate (PV) at 100 μM did not affect the biosensor, while the conductance of the biosensor was sharply decreased by the addition of amyl butyrate at 1 pM. This demonstrates that the biosensor of the present invention may detect odorants highly selectively.

Example 4

Identification of Inhibition of Non-specific Binding of Amyl Butyrate

To identify the inhibition of the non-specific binding of amyl butyrate, control experiments were performed.

Figure 12:
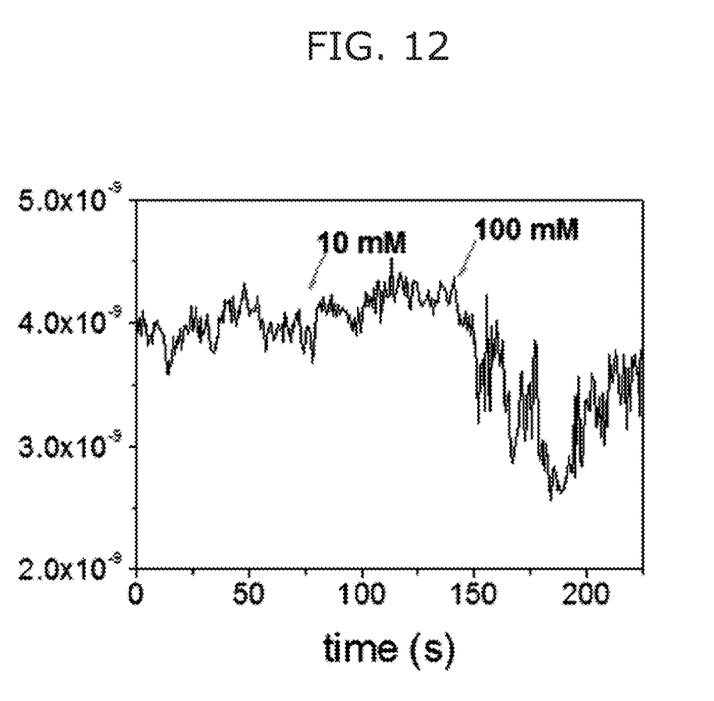
FIGS. 12 and 13 show graphs of a real time conductance measurement of the biosensors using modified carbon nanotube transistors with lipid membranes in which, hOR2AG1 is not included and bare carbon nanotube transistors, respectively.
Figure 13:
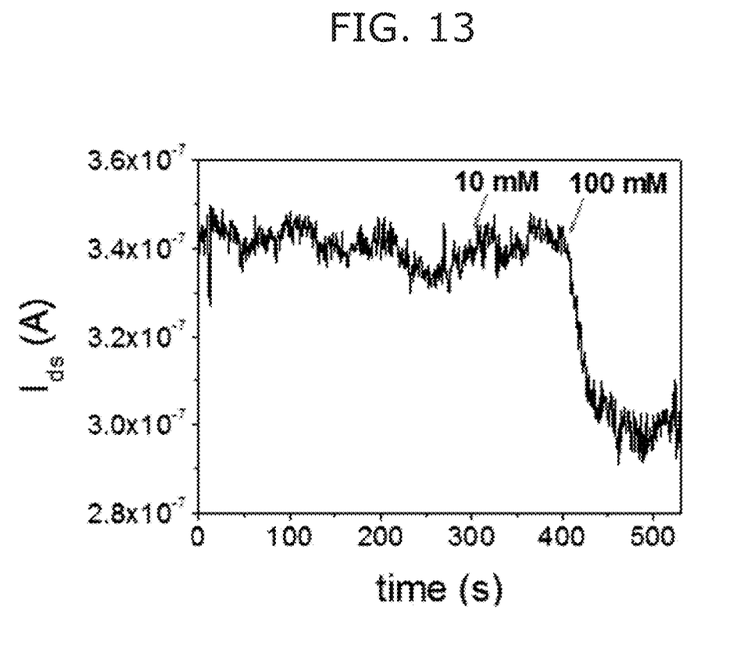

Amyl butyrate was introduced on modified carbon nanotube transistors with lipid membranes in which hOR2AG1 was not included (identical to those manufactured in Example 2 except that lipid membranes were formed but do not have hOR2AG1) and bare carbon nanotube transistors (identical to those manufactured in Example 2 except that lipid membranes having hOR2AG1 were not formed) to measure each of the conductance modulations. The results are shown in FIGS. 12 and 13, respectively. As shown respectively in FIGS. 12 and 13, each of the conductance modulations was observed on the biosensors using modified carbon nanotube transistors with lipid membranes in which hOR2AG1 was not included and bare carbon nanotube transistors, after the introduction of amyl butyrate at 100 mM. From the observations, it may be identified that for detection limits, 1012-fold higher concentrations were recorded when compared to the biosensors using hOR2AG1-functionalized transistors (See FIG. 10).

The following Table 1 shows the detection limits of the biosensors using carbon nanotube transistors for amyl butyrate in accordance with different surface modifications of carbon nanotube transistors as described above.

TABLE 1

| Surface Modification of Transistors | Detection Limit |
|---|---|
| Bare CNT | 100 mM |
| Lipid membranes without olfactory receptors | 100 mM |
| Lipid membranes with hOR2AG1 | 100 fM |

Example 5

Figure 14:
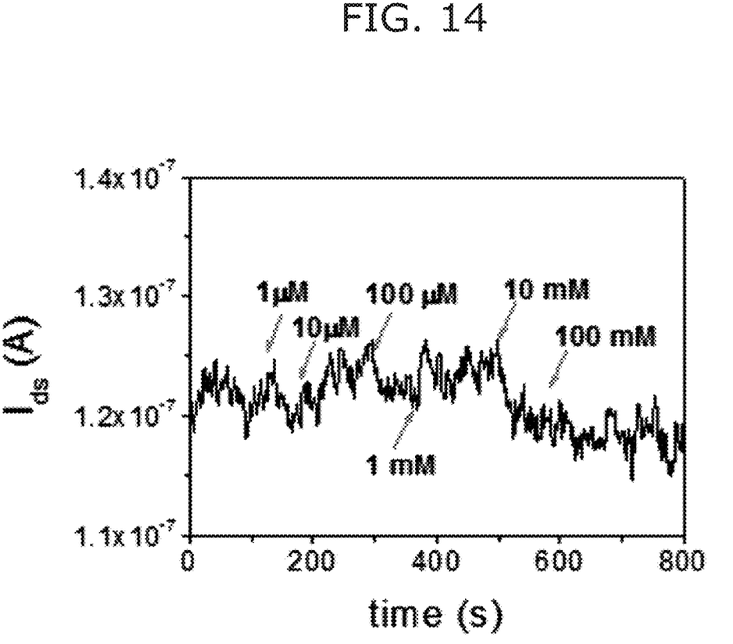
FIGS. 14 to 16 show graphs of a real time conductance measurement of the biosensors after butyl butyrate, pentyl valerate, and propyl butyrate were introduced at various concentrations, respectively, in accordance with Example 5.
Figure 15:
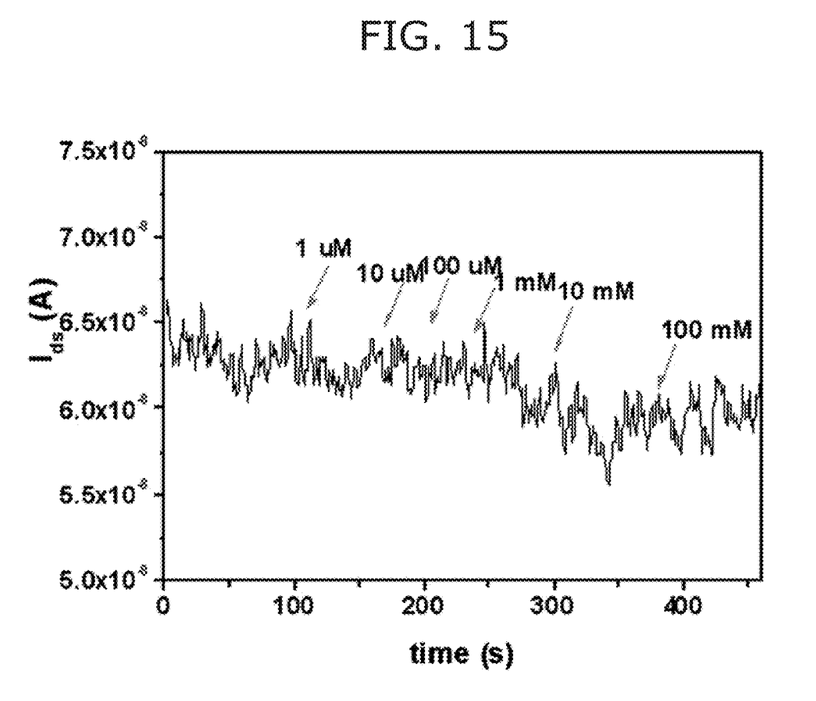
Figure 16:
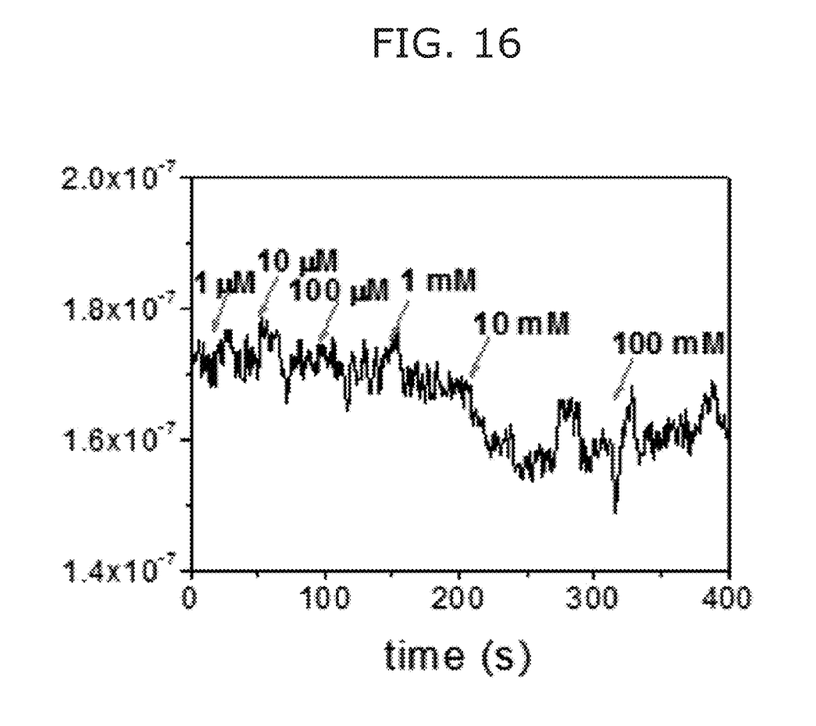

Identification of Selectivity of Biosensor Using Human Olfactory Receptor-Functionalized Transistors of the Present Invention Butyl butyrate, phenyl valerate, and propyl butyrate were introduced at various concentrations on the biosensors using hOR2AG1 functionalized transistors manufactured in Example 2 of the present invention, each of the conductance modulations was measured, and the results were recorded in FIGS. 14 to 16, respectively. The arrows illustrated in FIGS. 14 to 16 show time points of introduction of each odorant.

From FIGS. 14 to 16, it may be identified that conductance modulations were recorded after the introduction of butyl butyrate, phenyl valerate, and propyl butyrate at the concentration of 10 mM. The concentration is $10^{11}$ fold higher than that in the detection limit of the biosensor using hOR2AG1 functionalized transistors (See FIG. 10).

The following Table 2 shows the detection limits of the biosensors using carbon nanotube transistors of the present invention for various odorants.

TABLE 2

| Odorant | Detection Limit |
|---|---|
| Amyl butyrate (AB) | 100 fM |
| Propyl butyrate (PB) | 10 mM |
| Butyl butyrate (BB) | 10 mM |
| Pentyl valerate (PV) | 10 mM |

The present application contains subject matter related to Korean Patent Application No. 10-2008-0042373 and 10-2009-0039471, filed in the Korean Intellectual Property Office on May 7, 2008, and May 6, 2009, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

What is claimed is:

1. A transistor, comprising:
a substrate;
a source electrode and a drain electrode formed being spaced apart from each other on the substrate;
a nanostructure electrically contacted with and formed between the source electrode and the drain electrode; and
a lipid membrane having an olfactory receptor protein which is formed to cover surfaces of the source electrode, the drain electrode, and the nanostructure.

2. The transistor of claim 1, wherein the nanostructure is at least one form selected from the group consisting of nanotube, nanowire, nanorod, nanoribbon, nanofilm, and nanoball.

3. The transistor of clam 2, wherein the nanostructure is single-walled carbon nanotube.

4. The transistor of claim 1, wherein the olfactory receptor protein comprises a cysteine residue and changes from a neutral acid form to a negatively-charged base form when bound to specific odorants.

5. The transistor of claim 1, wherein the olfactory receptor protein is human olfactory receptor 2AG1 (hOR2AG1).

6. The transistor of claim 1, wherein the substrate is at least one selected from the group consisting of silicon, glass, quartz, metal, plastic and oxide.

7. The transistor of claim 1, wherein the source electrode and the drain electrode are formed as at least one metal selected from the group consisting of platinum, gold, chrome, copper, aluminum, nickel, palladium, and titanium.

8. A method for manufacturing a transistor, comprising:
forming a nanostructure on a substrate;
forming a source electrode and a drain electrode to be spaced apart from each other and electrically contact the nanostructure on the substrate and
forming a lipid membrane having an olfactory receptor protein to cover surfaces of the nanostructure, the source electrode, and the drain electrode.

9. The method of claim 8, wherein said forming a nanostructure on the substrate comprises patterning a self-assembled monolayer consisting of a molecule with a higher interface energy to the nanostructure than that of the substrate surface, on the substrate surface; immersing or exposing the patterned substrate in a nanostructure-containing solution or to a nanostructure-containing gas; and selectively adsorbing the nanostructure on a bare surface portion of the substrate on which the self-assembled monolayer is not formed.

10. The method of claim 9, wherein when the nanostructure is carbon nanotube, the molecule with a higher interface energy to the nanostructure than that of the substrate surface is at least one selected from the group consisting of octadecyltrichlorosilane (OTS), octadecyltrimethoxysilane (OTMS), octadecyltriethoxysilane (OTE), and octadecanethiol (ODT).

11. The method of claim 9, wherein said pattering a self-assembled monolayer is performed by microcontact printing, photolithography, dip-pen nanolithography, e-beam lithography, ion-beam lithography, nanograffing, nanoshaving, or STM lithography.

12. The method of claim 8, wherein said forming a source electrode and a drain electrode to be spaced apart from each other and electrically contact the nanostructure on the substrate is performed by photolithography, physical vapor deposition (PVD), e-beam evaporation, or thermal evaporation.

13. The method of claim 8, wherein said forming a lipid membrane having an olfactory receptor protein to cover surfaces of the nanostructure, the source electrode, and the drain electrode comprises spreading a solution of lipid membrane having the olfactory receptor protein on surfaces of the nanostructure, the source electrode, and the drain electrode, vacuum-drying the solution, and fixing the olfactory receptor protein.

14. The method of claim 8, wherein the nanostructure is at least one form selected from the group consisting of nanotube, nanowire, nanorod, nanoribbon, nanofilm, and nanoball.

15. The method of claim 14, wherein the nanostructure is single-walled carbon nanotube.

16. The method of claim 8, wherein the olfactory receptor protein comprises a cysteine residue and changes from a neutral acid form to a negatively-charged base form when bound to specific odorants.

17. The method of claim 8, wherein the olfactory receptor protein is human olfactory receptor 2AG1 (hOR2AG1).

18. A biosensor for detecting odorants to be bound to the olfactory receptor protein by using a transistor of claim 1.

19. A method for detecting odorants using a biosensor of claim 18, the method comprising:
exposing odorants to the biosensor of claim 18; and
measuring a conductance modulation generated by binding the odorants to the olfactory receptor protein of the biosensor.

20. The method of claim 19, wherein said exposing odorants to the biosensor of claim 18 is performed by contacting an odorant-containing solution or an odorant-containing gas with the biosensor.

* * * * *